United States Statutory Invention Registration [19]

[11] Reg. Number: H727

Pax [43] Published: Jan. 2, 1990

[54] PATIENT MONITORING DEVICE

[75] Inventor: George E. Pax, Albuquerque, N. Mex.

[73] Assignee: The United States of America as represented by the Secretary of the Air Force, Washington, D.C.

[21] Appl. No.: 198,951

[22] Filed: May 26, 1988

[51] Int. Cl.[4] ..... G06F 15/42

[52] U.S. Cl. ..... 364/413.05; 364/413.06

*Primary Examiner*—Thomas H. Tarcza
*Assistant Examiner*—Linda J. Wallace
*Attorney, Agent, or Firm*—William G. Auton; Donald J. Singer

[57] ABSTRACT

A data acquisition system receives, stores, and displays signals from multiple medical sensors. The medical sensors serve as a source of analog input signals which are measures of certain body conditions. The signals are fed to a gain network and then to low pass and high pass filters. They are converted from analog to digital signals in a A/D converter. A microprocesor processes the input signals and the control signals to provide analog output signals. A display furnishes a visual indication of the monitored body conditions.

6 Claims, 4 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PATIENT MONITORING DEVICE

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to monitoring systems, and more specifically to a computer controlled data acquisition system capable of monitoring multiple life functions simultaneously.

The purpose of the invention is to collect a data base such that the requirements and processing necessary for a field patient monitor system could be defined.

Data acquisition systems of various types have been proposed in the prior art.

SUMMARY OF THE INVENTION

The present invention is a data acquisition device which monitors multiple signals simultaneously using: a plurality of acquisition modules, a housing, a plurality of digital arrays, a system clock, a microprocessor system controller, a digital signal bus, and a display. Each acquisition module can be connected to and receive analog signals from most conventional sensors which monitors a function. Such conventional sensors include standard EKG and EEG units used in hospitals. The acquisition module provides adjustable gain and filtering to the analog signals and converts it to a digital signal.

The housing used in a plurality of commercially available Computer Automated Measurement and Control (CAMAC) crates which house and supply power to all modules. In one embodiment of the invention, six crates are used to house: sixty four acquisition modules, one clock module, and six dataways.

The clock module provides a system clock signal to synchronize all of the acquisition modules. Each CAMAC crate includes one dataway to interconnect all of the acquisition modules in the crate. The digital signal bus is a commercially available IEEE-488 bus which conducts the digital signals from the six dataways to a host system controller.

The system controller processes the digital data signals it receives from the bus in order to store, print and display the data from up to sixty four different medical sensors. The system controller is any commercially available computer with a disk drive, such as: Hewlett Packard's model HP220T, model HP9122D, or model HP797OE.

In one embodiment of the invention, a single oscilloscope is used as the display. The oscilloscope used is a Tektronix 2213, dual trace oscilloscope which may be connected directly to the output ports of any selected acquisition module to display signals of interest.

It is an object of the present invention to provide a data acquisition system which monitors multiple life functions from a variety of medical sensors simultaneously.

It is another object of the present invention to combine diverse functions into a single computer controlled unit.

These objects together with other objects, features and advantages of the invention will become more readily apparent from the following detailed description when taken in conjunction with the accompanying drawings wherein like elements are given like reference numerals throughout.

DETAILED DESCRIPTION OF THE PREFERRED EMBODIMENT

The present invention is a data acquisition device especially devised to monitor multiple functions simultaneously, and to combine diverse functions into a single computer controlled unit.

Figure 1:
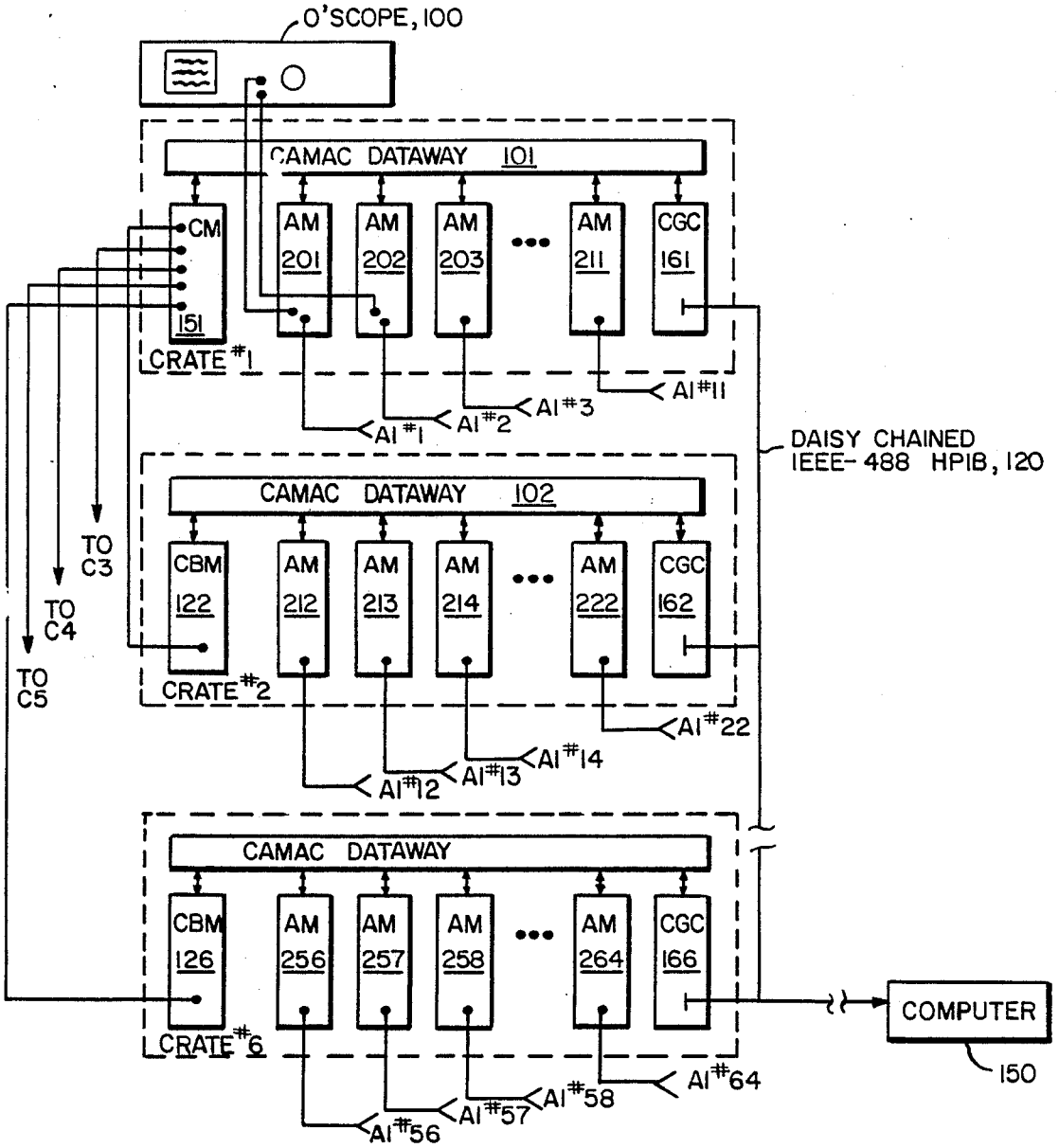
FIG. 1 is a block diagram of the present invention.

The reader's attention is now directed towards FIG. 1, which is a block diagram of an embodiment of the patient monitoring system. FIG. 1 depicts: the oscilloscope display 100, CAMAC crates (C) 1, 2 and 6, CAMAC dataways, 101, 102 and 106, a plurality of acquisition modules (AM) 201–264, a single clock module (CM) 151, CAMAC-to-controller (CGC) modules 161–166, clock buffer modules (CBM) 122–126, digital data bus 120, and the control computer 150. The functions of each of these units is described below.

As shown in FIG. 1, most of the equipment is housed on an equipment rack in a plurality of commercially available Computer Automated Measurement and Control (CAMAC) crates. The system of FIG. 1 actually uses 6 CAMAC crates with a total of sixty four acquisition modules. Since crates 2–5 are identical, it was deemed unnecessary to depict all of them in the figure. These crates house, cool and supply electrical power to all modules, including the acquisition modules, which electrically connect with and receive analog signals from 64 conventional medical sensors, denoted as AI #1–AI#64. Note that in the system of FIG. 1, five of the crates hold 11 acquisition modules, while the sixth holds 9 for a total of 64. The crates are illustrated further in a subsequent figure discussed below.

In the system of FIG. 1, a single oscilloscope 100 is used as the display. The oscilloscope is a Tektronix 2213 dual trace oscilloscope, which may be connected directly to the output ports of any selected acquisition module to display signals of interest.

As mentioned above, each acquisition module can be connected to and receive analog signals from most conventional sensor which monitors a particular life functon of a patient. Such conventional sensors include standard EKG and EEG units used in hospitals. The acquisition module provides adjustable gain and filtering to the analog signals and converts it to a digital signal for input into the microprocessor 150. Each acquisition module also reconverts the filtered processed digital signal back into analog for sampling by the oscilloscope 100 when required. Unlike the CAMAC crates, all acquisition modules are identical and interchangeable. An example of an acquisition module is discussed in more detail below.

The clock module 151 provides a system clock signal to synchronize all of the acquisition modules. Each CAMAC crate includes one dataway to interconnect all of the acquisition modules in the crate. The digital signal bus is a commercially available IEEE-488 bus 120, which conducts the digital signals from the six dataways to a host system controller 150.

The system comptroller 150 processes the digital data signals it receives from the bus in order to store, print and display the life functions from up to sixty four different medical sensors. The system controller 150 is any suitable commercially available computer with a disk drive, such as: Hewlett Packard's model HP2207, model HP9122D, or model HP797OE.

Figure 2:
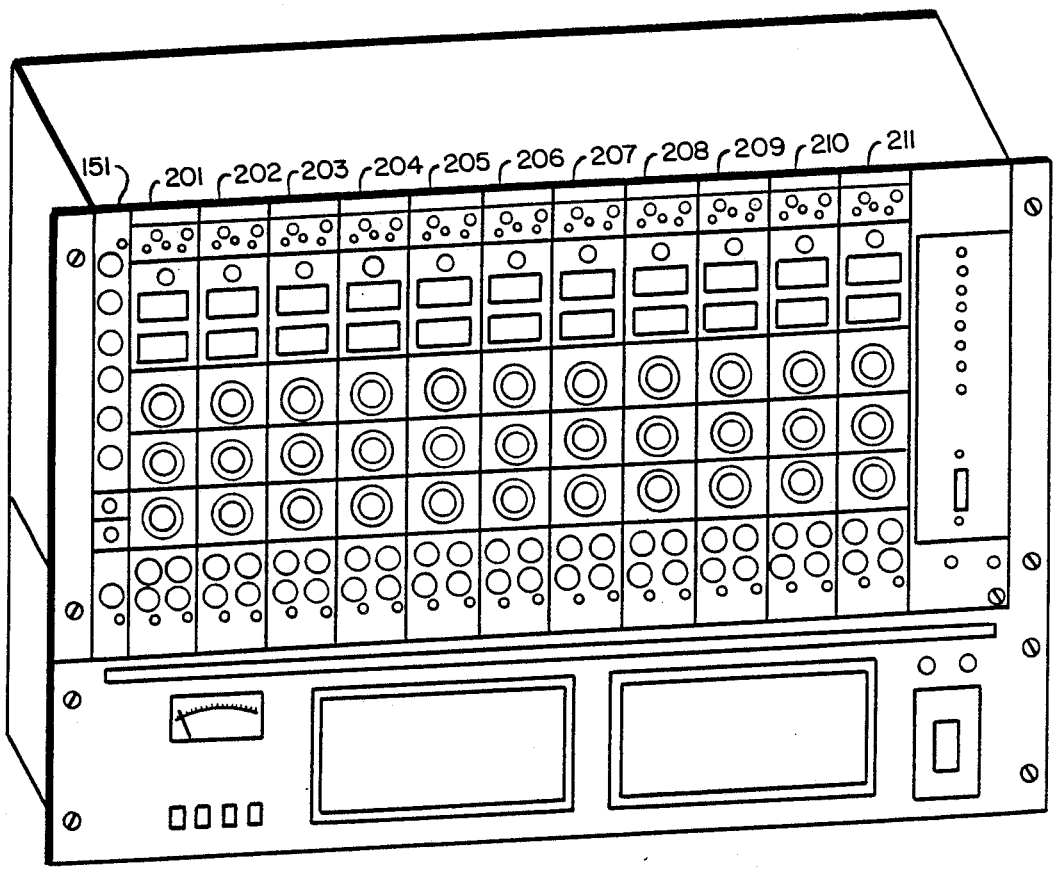
FIG. 2 is an illustration of a crate used in the system of FIG. 1.

FIG. 2 is an illustration of the first crate used in the system of FIG. 1 when it contains the equipment of the present invention. Each CAMAC crate, as off-the-shelf equipment, is a 19-inch rack mountable frame which houses, powers, cools and provide dataway communication for CAMAC modules. The crate has 25 positions for modules which plug into a backplane. The backplane is called the CAMAC dataway. The dataway is a multilay printed circuit board (PCB) which transfers command, data, status and address data between the modules as well as providing power supply buses. As adapted. for the present invention, the crate of FIG. 2 holds eleven acquisition modules 201–211, and a single clock module 151.

Figure 3:
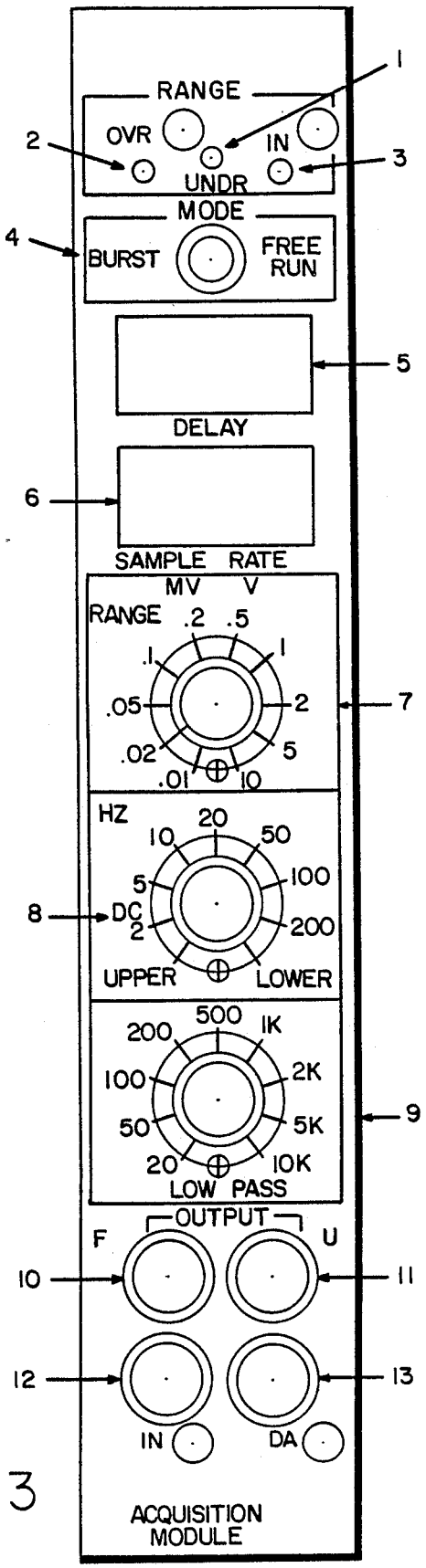
FIG. 3 is an illustration of the front panel of an acquisition module used in the system of FIG. 1.

FIG. 3 is a detailed illustration of the front panel of an acquisition module.

Located at the top of the front panel are the Light Emitting Diodes (LEDs) 1–3. They indicate the range of the input signal. The in-range LED 3 is green, the over-range LED 2 is red and the under-range LED 1 is yellow. The under-range LED 1 indicates that the analog signal is below 10 percent of full scale for periods of 1 second or longer. The over-range LED 2 indicates that the analog signal has peaks above 90 percent of scale at periods of 1 second or more. Finally, the in-range LED 3 ion indicates the exclusion of under-range and over-range. One of the LEDs 1–3 should be on at all times.

Below the LEDs 1–3 is the mode switch 4, which allows manual selection of either Burst or Continuous Mode data acquisition. This switch defines which mode will be used to sample data. Burst mode fills one buffer of 65,356 samples and then stops. In continuous mode, the first and second buffers are filled alternately. No precaution is taken to prevent overwriting of data.

The delay and sample rate thumbwheel switches 5 and 6 allow manual selection of 1 to 999 clock periods between the start of data collection and the first sample (delay) and the time between samples (sample rate). The delay interval thumbwheel 5 is a three-digit BCD encoded thumbwheel which defines the number of clock intervals to wait before sampling starts. The system always waits at least one interval, therefore, a count of zero is treated as one. When this input is overridden by the host system controller, the count is extended to $2^{16}-1$ or 65,535 clock intervals as the maximum possible.

The sample interval thumbwheel 6 is a three digit BCD encoded thumbwheel which defines the number of clock intervals to wait between samples. Zero is not reasonable and is treated as a one. The interval can be as high as 65,535 clock intervals (via host over-ride).

The range select switch 7 is a dual select switch which defines which voltage represents full scale. The steps are in a 1, 2, 5 sequence starting at 10 microvolts and going to 10 volts. The inside knob changes the scale from reading millivolts to reading volts.

The high pass filter cutoff 8 (3 dB point) is a dual shaft rotary switch. The scale is in hertz. When the smaller knob is turned fully counterclockwise, the lower number is used.

The low pass filter cutoff 9 is a 9 position rotary switch read in hertz. It defines the 3 dB point of the low pass filter cutoff. Finally, there are four coax connectors at the bottom of the module. One is for the analog input. The other three allow observation of the acquired waveform after amplification but before filtering, after amplification and filtering and of a digital to analog (D to A) converted representation of the output digital data. The filtered output 10 is the analog signal at the output of the filters and following the gain section. This output is used for operator inspection and verification.

The unfiltered output 11 is the analog signal following the gain section. This output is used for operator inspection and verification. The analog input 12 is the point where the input of analong signals from conventional medical sensors. The digital-to-analog output 13 is the output of the digital-to-analog convertor.

Table 1, presented below, is a table of specifications for each acquisition module used in the present invention.

TABLE 1

| SPECIFICATIONS AND ACQUISITION MODULE | |
|---|---|
| Power | +6 VDC @ AMPS |
| | +24 VDC @ 200 MA |
| Size | Double Wide Module |
| Weight | 5 Pounds |
| Sampling Clock | 1 to 10 KHertz |
| Sampling Interval | .1 to 100 Milliseconds @ 10 KHz |
| From Front Panel | 1 to 1000 Milliseconds @ 1 KHz |
| Remote | .001 to 6.5 Seconds @ 10 KHz |
| | .001 to 65 Seconds @ 1 KHz |
| Low Pass Filter | |
| Type | Butterworth |
| Poles | 4 |
| Minimum Cutoff | 20 Hz |
| Maximum Cutoff | 10 KHz |
| High Pass Filter | |
| Type | Butterworth |
| Poles | 4 |
| Minimum Cutoff | .02 Hertz (DC Available) |
| Maximum Cutoff | 200 Hertz |
| Input | |
| Ranges | 10 Microvolts to 10 Volts |
| Sequence | 1, 2, 5 |
| Impedance | 1 Megohm |
| Noise | 10 MV RMS |
| Accuracy | 1% @ 10 Volts |
| Offset | 1 MV @ 10 Volts |
| Indicators | Over Range, Under Range, In Range |
| Controls | Delay Intervals |
| | Sample Intervals |
| | Low Pass Cutoff Frequency |
| | High Pass Cutoff Frequency |
| | Input Range |
| Sampling Memory | 2 Buffers of 128 kBytes Each |

Figure 4:
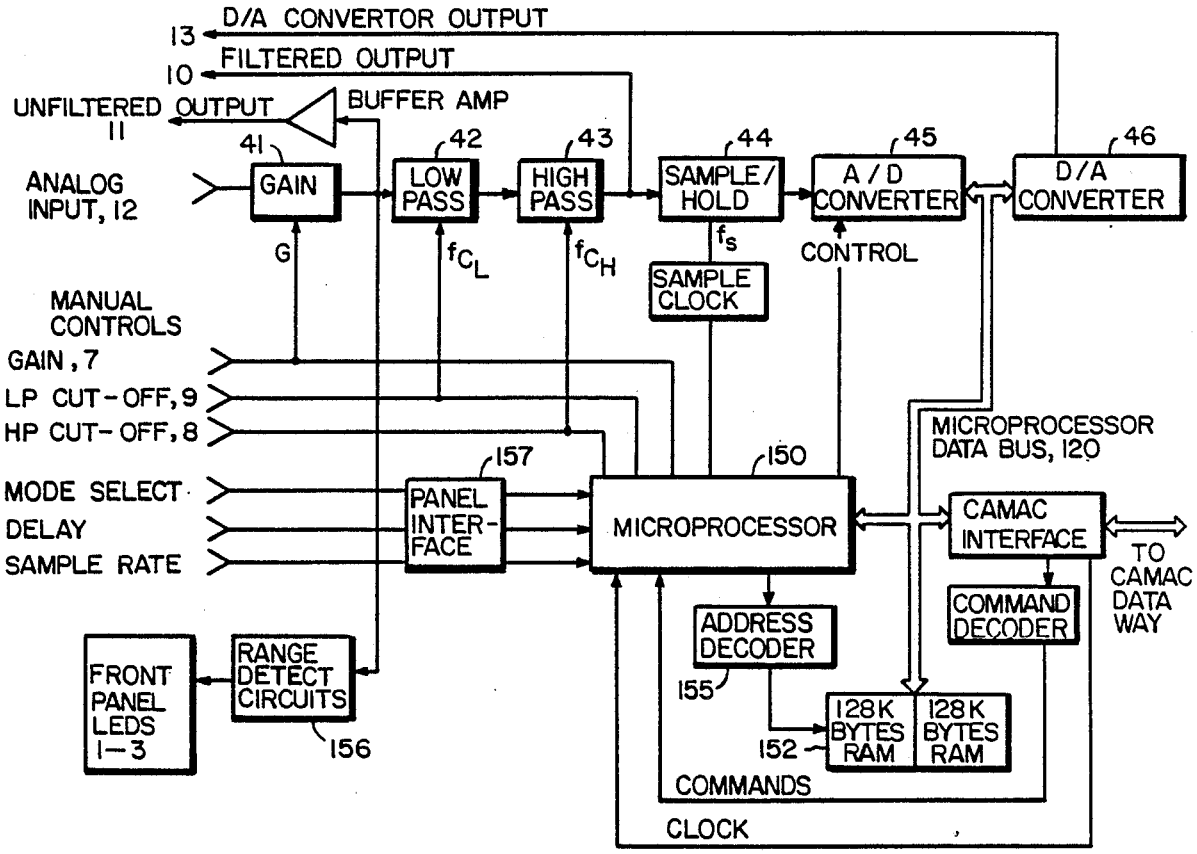
FIG. 4 is a functional block diagram of the acquisition module elements.

FIG. 4 is a functional block diagram of the acquisition module elements as they interact with the rest of the invention. As depicted in FIG. 4, received analog signals are processed with: adjustable gain 41, high and low pass filtering 42-43, sampling 44, and conversion into digital before being forwarded to the microprocessor 150. FIG. 4 also depicts the sources of the three analog outputs 10, 12, and 13 shown in FIG. 3. Also depicted are the interconnections of the manual controls for the gain 7, and high and low pass filtering 8, 9 respectively with the adjustable amplifier 41 and filters 42-43. The specifications for these elements is as presented in Table 1, and is deemed to be sufficient to enable one skilled in the art to practice this aspect of the invention. The system of FIG. 4 is an acquisition module which is designed to operate from a sample clock of from 1 to 10 kilohertz. However, it is expected to operate with clock rates down to about 700 hertz and as high as 15 kilohertz. It has a programmable delay of from 1 to 999 sample clock periods from the front panel. This delay can be remotely extended to as high as 65, 535 sample clock intervals. The same is true of the interval between samples. The high pass and low pass filters are both four-pole Butterworth filters. The highest full-scale input range is ±10 volts.

Figure 5:
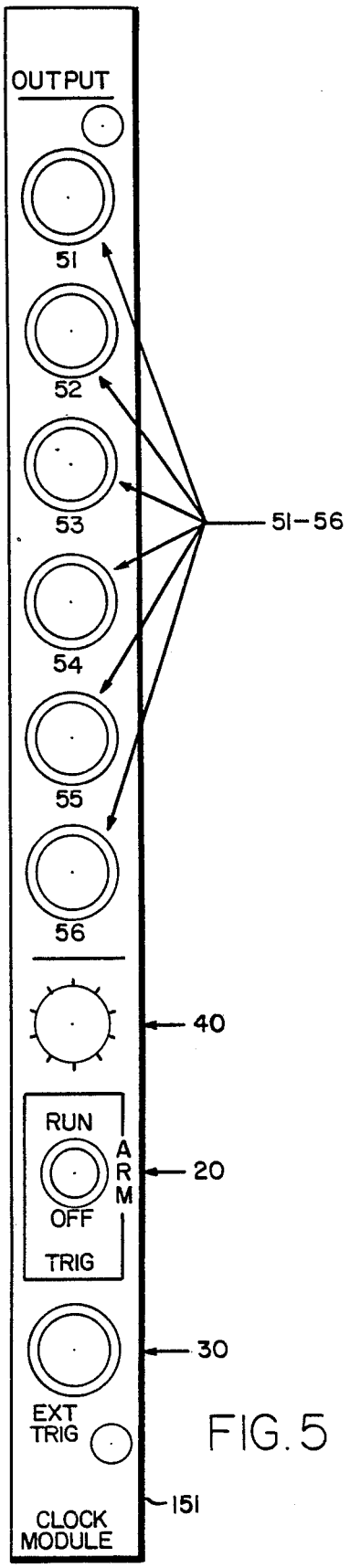
FIG. 5 is an illustration of the front panel of the clock module used in the system of FIG. 1.

FIG. 5 is an illustration of the front panel of the clock module 151 used in FIG. 1. The clock module is a stable, selectable clock pulse source which is a 10 megahertz crystal oscillator whose output is counted down to one of 10 frequencies (1 to 10 kHz in steps of 1 kHz point where the input of analog signals from conven- ıe CAMAC dataway and to front panel output connectors 51–56. Output connectors 51–56 are each intended to drive a crate in the system. A frequency select switch 40 entails a rotary switch which selects the clock frequency. Frequencies that are available are from 1 to 10 kilohertz in 1 kilohertz steps.

A trigger 20 has a run, an arm, and an off position. In the off position, the clock is not running and the outputs are low. In the run position, the outputs are running at the selected frequency. In the arm position, the clock may or may not be running. If it is not running, it may be started by a closure on the external trigger input. Also, in the arm position, the host computer may start and stop the clock remotely.

The external trigger 30 is used as follows. In the arm condition and with the clock stopped, the clock may be started by a switch closure on this input. This input will normally have a coaxial cable connected to it and will be terminated with a momentary switch.

Table 2 is a list of the technical specifications required for the clock module. It is believed that this information enables one skilled in the art to practice this aspect of the invention.

TABLE 2

| CLOCK MODULE SPECIFICATIONS | |
|---|---|
| Power | +6 VDC @ 200 ma |
| Size | Single Wide CAMAC Model |
| Weight | 2 lbs |
| Output Clock | 1 kilohertz to 10 kilohertz |
| Outputs | 6 TTL level outputs |
| Control | Run, stop, and arm control from the front panel remotely programmable to run or stop when front panel is set to arm. |
| Accuracy | .1% |

The buffer module 122 of FIG. 1 merely buffers the clock signal to restore signal integrity and to drive the dataway backplane. Its specifications are shown in Table 3.

TABLE 3

| BUFFER MODULE SPECIFICATIONS | |
|---|---|
| Power | 6 VDC @ 50 ma |
| Size | Single wide CAMAC module |
| Weight | 2 lbs |
| Input | TTL |
| Output | TTL |

The CAMAC to GPIB modules 161–166 used in FIG. 1 are off-the-shelf LeCroy Model 8901 interface elements. As indicated in FIG. 1, each of the CGC modules 161–166 provides a link between the GPIB-/IEEE Standard 488–1975 and the CAMAC/IEEE Standard 585–1975 buses.

As mentioned above, the CAMAC dataways 101–106 as well as the digital data bus 120 are all commercially available over-the-shelf items which have been identified above. Similarly, the host system controller 150 of FIG. 1 is a commercially available computer produced by Hewlett Packard.

The present invention is operated as follows. The first step is to decide on a frequency for the the sample clock. This is selected by the frequency switch 40 on the front of the clock module. This should be based on the maximum frequency expected to be captured from any channel. It is good practice to have the sample frequency at least 4 to 6 times the highest frequency component in the sampled signal.

Next, the high pass filters on each acquisition module should be set to attenuate frequencies above the range of interest. If the frequency content of the channel to be set up is less than the maximum that determined the frequency of the clock module, it may be desireable to reduce the sample rate of the channel. This is done by setting the thumbwheel switches labeled "SAMPLE". 000 and 001 have the same result. The acquisition module samples every 1 clock period. If the thumbwheel is set at 2, the acquisition module samples every 2 clock periods. For the maximum case (999), the acquisition module samples every 999 clock periods.

The "delay" thumbwheel functions similarly to the "sample" thumbwheel. The delay only extends the time between the first clock and the first sample. After the delay has time out, the sample interval is initiated. Following termination of the first sample interval, the first sample is taken.

Once the sample interval and delay interval have been set, the mode should be based in part on the system controlling the acquisition unit. For the stand alone case, the recommended mode used should be the Burst mode. The Burst mode records data in one half the available memory (65,000 samples). Once this memory area is full, sampling stops. The system will not sample again unless the sample clock is stopped and restarted. When the system is restarted, the samples are stopped in the other half of the memory. Premature termination of the sample clock will also cause the system to swap to the other buffer for the next acquisition.

The FREE-RUN mode only makes sense for an acquisition system with an host system controller. In this mode, there are still two buffers but the system does not stop when it reaches the end of a buffer. It goes ahead to the next buffer even if there is data in the buffer which has not been returned to the external data handler. This requires the external data handler to unload data at an equivalent rate to the sampling rate. The limiting factor will probably be dependent on the performance of the host system controller, not he acquisition system.

The range setting logically follows next. The operator's knowledge of the signal to be captured is important here. Typical sensors used with the invention include the EEG and EKG, the output frequencies of which are known to the users. When connected to a particular acquisition module, the low pass filter of the acquisition module should be set to cut off frequencies below the range of interest.

After the system is powered up, it is controlled through the IEEE-488 controller, mentioned above. The controller is not complex. It contains registers that, when activated, drive the various signals on the CAMAC backplane called the dataway. Most of the control is concerned with loading these registers and initiating cycles. Further information on the CAMAC controller (IEEE-488) can be found in the instruction manual for the LeCroy 8901 controller. The host system controller 150 merely receives and stores up to 64 separate inputs into the random access memories, and is essentially a post office with 64 mailboxes.

As mentioned above, the patient monitoring system is designed to be a flexible data acquisition system. It is built as a modular system where each data acquisition channel is a separate module. The interconnection between the channels is provided by the commercially available CAMAC crate, and control is provided by the commercially available CAMAC controller. The data acquisition module, the clock module which synchronizes the individual channels, and the buffer module which buffers the clock signal all expand the system beyond one crate.

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. A data acquisition system comprising:

a plurality of inputs, each of which is capable of monitoring a life function of a patient and outputting analog signals indicative of acquired signals;

a means for processing said analog signals, from said plurality of inputs, into filtered digital signals, said processing means filtering said analog signals to attenuate unwanted frequencies above and below a range of interest to produced filtered analog signals, said processing means converting said filtered analog signals into said filtered digital signals;

a memory which receives and stores said filtered digital signals;

a means for controlling the data acquisition system, said controlling means receiving and conducting the filtered digital signals from the processing means to the memory; and a means for displaying the analog signals, said displaying means being electrically connected with and displaying said analog signals received by said processing means.

2. A data acquisition system, as defined in claim 1, wherein said processing means comprises:

a plurality of acquisition modules, each being electrically connected with and receiving said analog signals from one of said plurality of inputs, said acquisition modules producing said filtered analog signals by filtering said analog signals, and producing said filtered digital signals by converting into digital said filtered analog signals;

a clock module which produces clock signals used to coordinate the production of filtered digital signals by the plurality of acquisition modules;

a housing which cools, powers and houses said plurality of acquisition modules and said clock module; and at least one digital dataway fixed in said housing to receive, coordinate and output said clock signals and said filtered digital signals from said acquisition modules and said clock module to said controlling means.

3. A data acquisition system, as defined in claim 2, wherein each of said plurality of acquisition module comprises:

a first coaxial connector which electrically connects with and receives said analog signals from one of said inputs;

an amplifier which receives and amplifies said analog signals to produce amplified analog signals;

a low pass filter with an adjustable frequency cutoff to remove undesired low-frequency noise from received signals, said low pass filter producing output signals by receiving and filtering said amplified analog signals from said amplifier;

a high pass filter with an adjustable frequency cutoff which produces said filtered analog signals by receiving and filtering said output signals from said low pass filter;

an analog-to-digital converter which produces said filtered digital signals by processing said filtered analog signals from said high pass filter; and a plurality of second coaxial connectors which are connected to said amplifier, said low pass filter and said high pass filter to output signals to said displaying means.

4. A data acquisition system, as defined in claim 3, wherein said controlling means comprises:

a microprocessor bus which receives and conducts said clock signals and said filtered digital signals from each of said digital dataway in said processing means; and a microprocessor which receives said clock signals and said filtered digital signals from said microprocessor bus, and, stores said filtered digital signals in said memory.

5. A data acquisition system, as defined in claim 4, wherein said displaying means comprises an oscilloscope which receives and displays said analog signals from one of said second coaxial connectors of one of said acquisition modules.

6. A data acquisition system, as defined in claim 5, wherein said plurality of second coaxial connectors in each of said acquisition modules comprises:

an unfiltered coaxial connector output which electrically connects the amplifier to the oscilloscope so that it can display an unfiltered version of the analog signals; and a filtered coaxial connector output which electrically connects said high pass filter to the oscilloscope so that it can display a filtered version of the analog signals.

* * * * *